(12) United States Patent
Lunn et al.

(10) Patent No.: US 10,159,477 B2
(45) Date of Patent: Dec. 25, 2018

(54) ANCHOR ASSEMBLY

(71) Applicant: Smith & Nephew, Inc., Memphis, TN (US)

(72) Inventors: Richard M. Lunn, Kingston, MA (US);
David A. Paulk, Hopedale, MA (US);
Thomas C. May, Wrentham, MA (US);
Steven W. Astorino, Norfolk, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 15/137,050

(22) Filed: Apr. 25, 2016

(65) Prior Publication Data

US 2016/0235397 A1 Aug. 18, 2016

Related U.S. Application Data

(63) Continuation of application No. 12/259,106, filed on Oct. 27, 2008, now Pat. No. 9,345,467.

(60) Provisional application No. 60/982,521, filed on Oct. 25, 2007, provisional application No. 60/986,342, filed on Nov. 8, 2007.

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0403* (2013.01); *A61B 2017/044* (2013.01); *A61B 2017/0409* (2013.01); *A61B 2017/0412* (2013.01); *A61B 2017/0414* (2013.01); *A61B 2017/0427* (2013.01); *A61B 2017/0445* (2013.01); *A61B 2017/0453* (2013.01); *A61F 2002/0829* (2013.01); *A61F 2002/0888* (2013.01)

(58) Field of Classification Search
CPC .... A61B 2017/1142; A61B 2017/0453; A61B 2017/0412; A61B 2017/0414; Y10T 24/3653; Y10T 24/3967; F16G 11/048
See application file for complete search history.

(56) References Cited

U.S. PATENT DOCUMENTS

| | | | | |
|---|---|---|---|---|
| 5,100,417 A | * | 3/1992 | Cerier | A61B 17/0401 606/139 |
| 5,957,953 A | * | 9/1999 | DiPoto | A61B 17/0401 606/232 |
| 6,436,142 B1 | * | 8/2002 | Paes | A61B 17/8615 623/17.15 |
| 8,202,295 B2 | * | 6/2012 | Kaplan | A61B 17/0401 606/232 |
| 8,545,535 B2 | * | 10/2013 | Hirotsuka | A61B 17/0401 606/232 |
| 8,702,754 B2 | * | 4/2014 | DiMatteo | A61B 17/0401 606/232 |
| 9,636,100 B2 | * | 5/2017 | Wyman | A61B 17/0401 |
| 9,936,939 B2 | * | 4/2018 | Nguyen | A61B 17/0401 |

(Continued)

*Primary Examiner* — David Bates
(74) *Attorney, Agent, or Firm* — Norman F. Hainer, Jr.

(57) ABSTRACT

The present disclosure relates to an anchor assembly. The anchor assembly includes an anchor defining a cavity and an opening to the cavity and an insertion member configured for arrangement within the anchor cavity. The insertion member may include a body having a proximal end portion and a flat distal end portion. A method of tissue repair and other anchor assemblies are also disclosed.

64 Claims, 7 Drawing Sheets

(56) References Cited

U.S. PATENT DOCUMENTS

| | | | |
|---|---|---|---|
| 2006/0058800 A1* | 3/2006 | Ainsworth | A61B 17/70 606/86 A |
| 2007/0203498 A1* | 8/2007 | Gerber | A61B 17/0401 606/328 |
| 2009/0157124 A1* | 6/2009 | Ferragamo | A61B 17/0401 606/301 |
| 2011/0004242 A1* | 1/2011 | Stchur | A61B 17/0401 606/232 |
| 2011/0112576 A1* | 5/2011 | Nguyen | A61B 17/0401 606/232 |

* cited by examiner

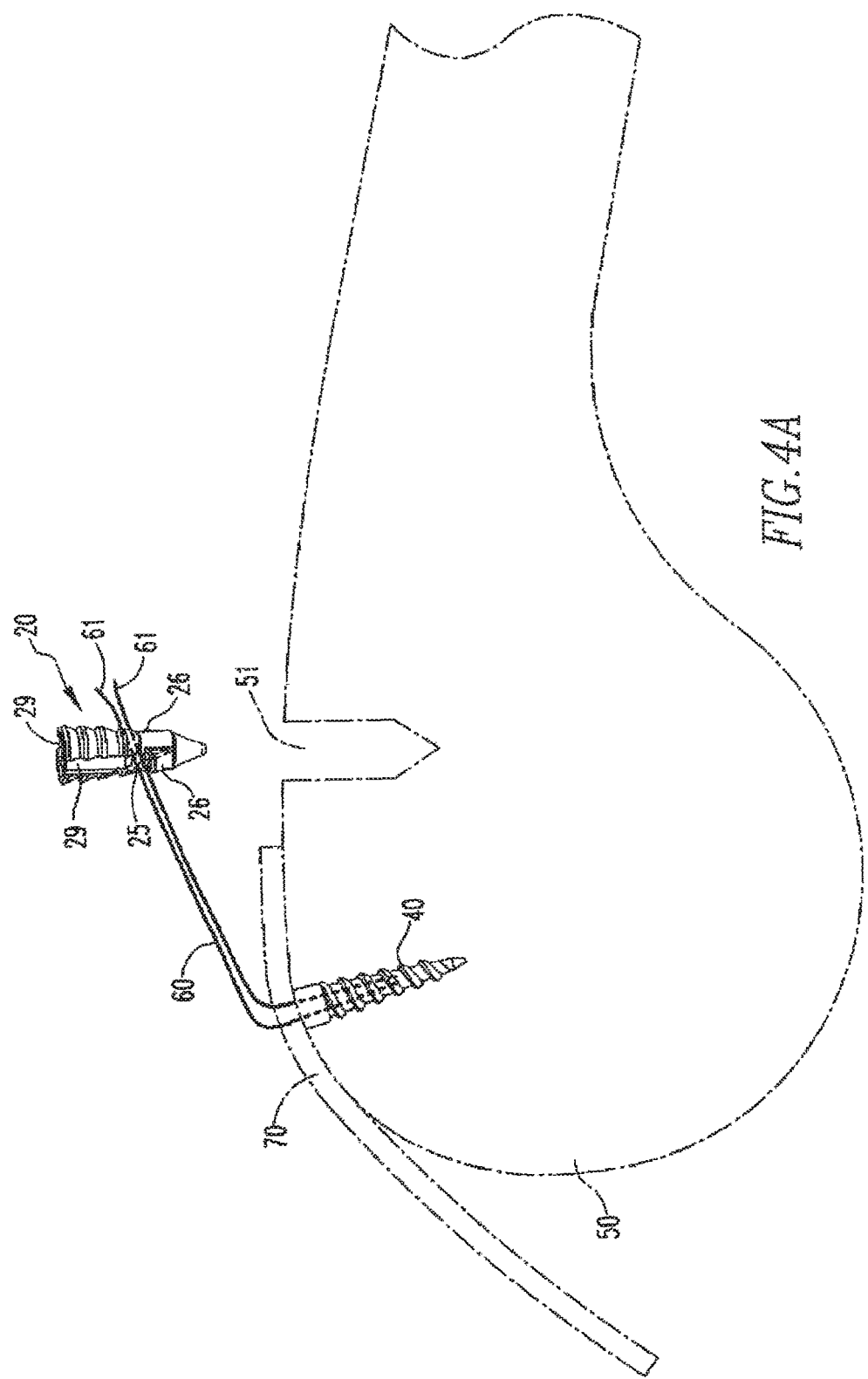

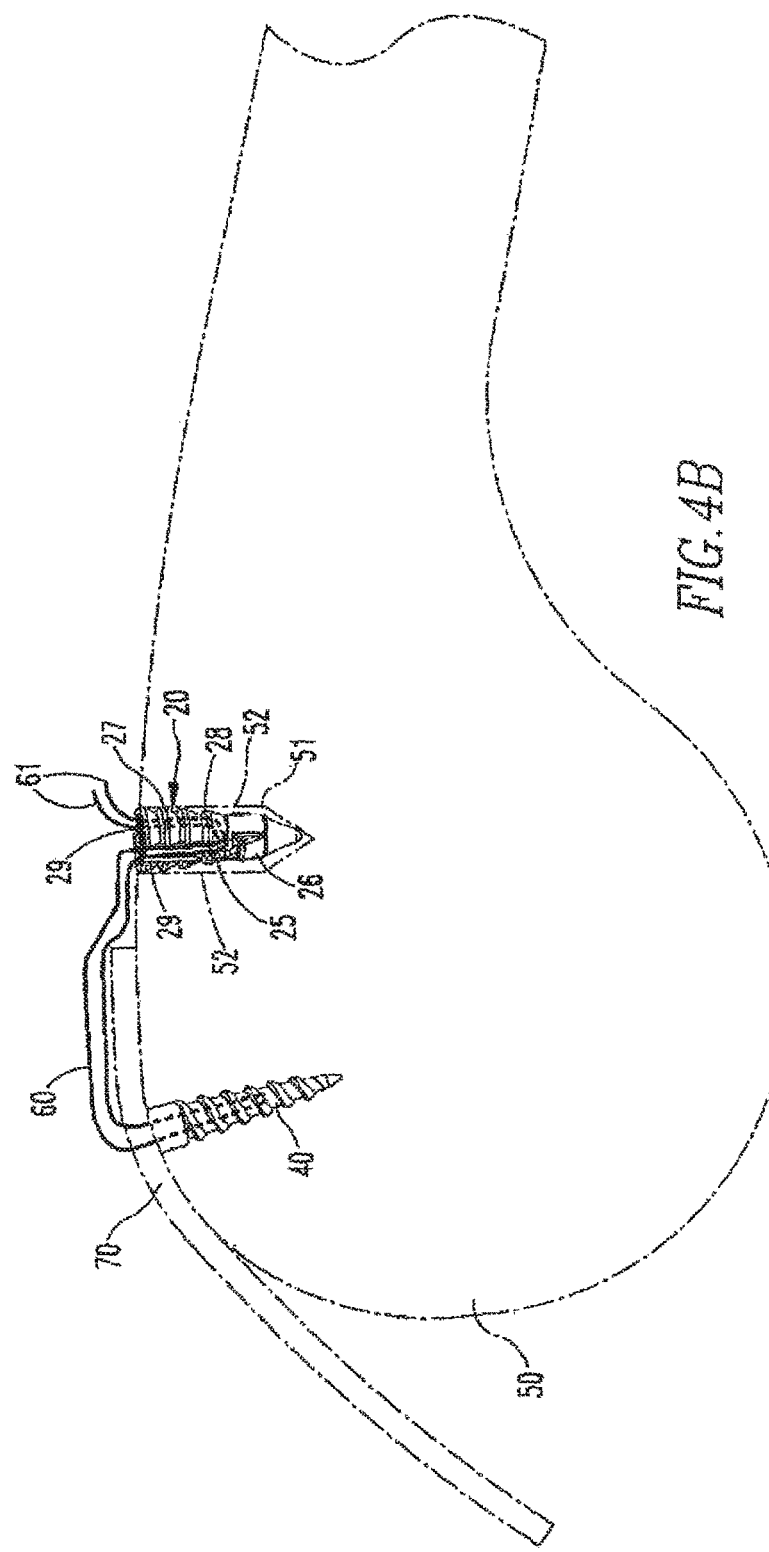

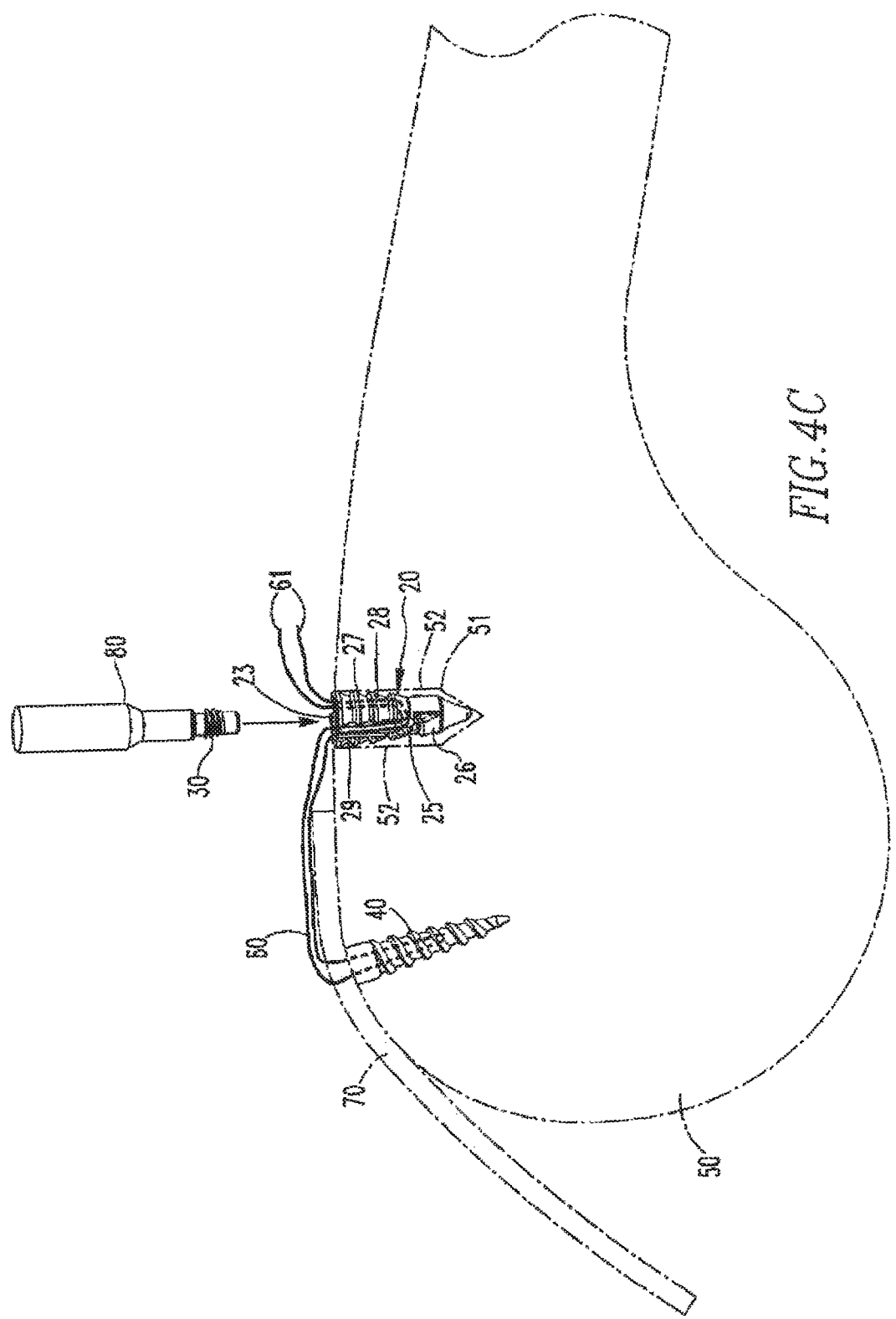

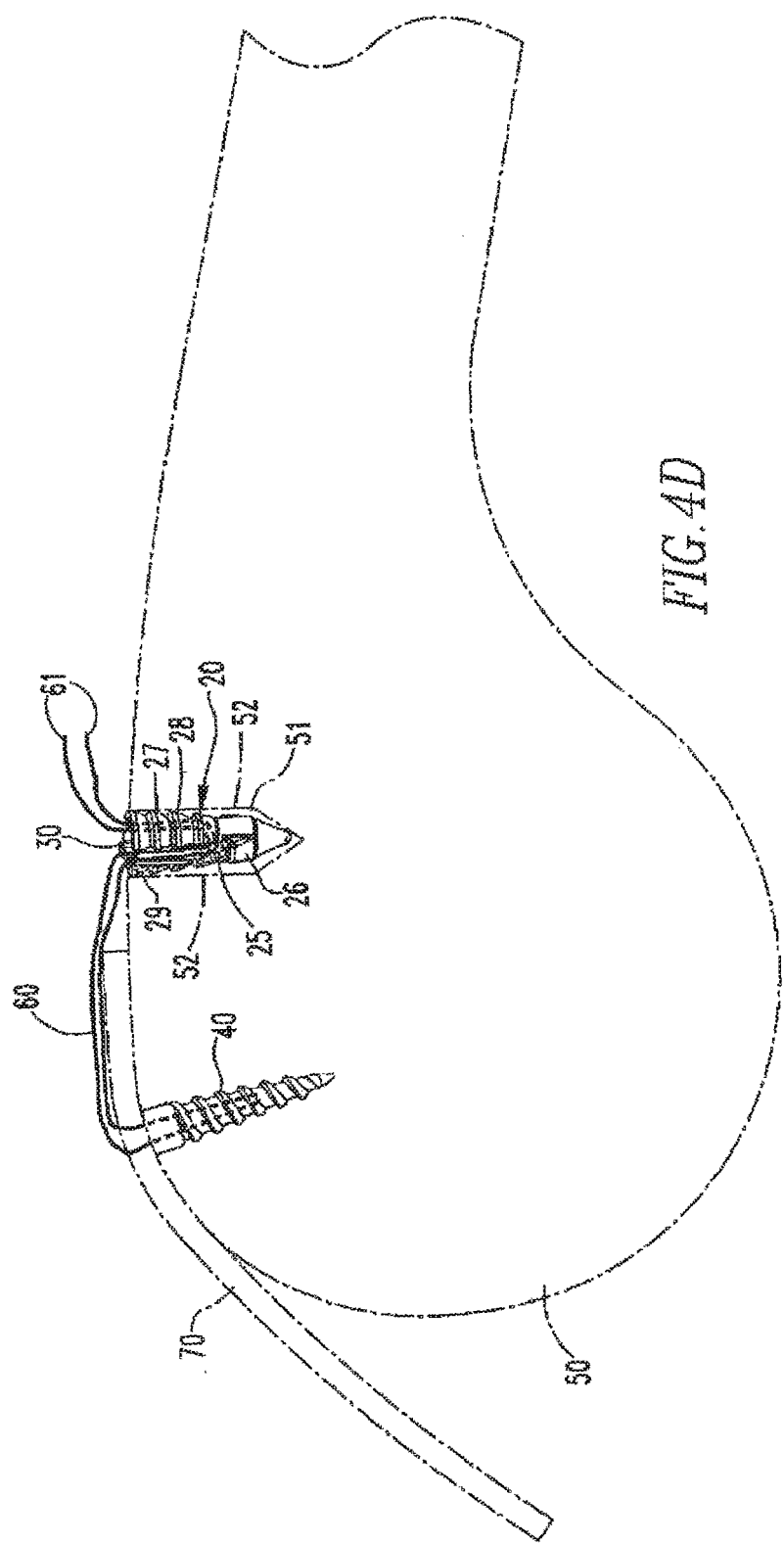

ANCHOR ASSEMBLY

CROSS-REFERENCE TO RELATED APPLICATIONS

This application is a continuation of U.S. patent application Ser. No. 12/259,106 filed on Oct. 27, 2008 which claims the benefit of U.S. patent application Ser. No. 60/982,521 filed on Oct. 25, 2007 and U.S. patent application Ser. No. 60/986,342 filed on Nov. 8, 2007, all of the disclosures of which are incorporated herein by reference in their entirety.

BACKGROUND

Field of Technology

The present disclosure relates to tissue repair, and more specifically, to an anchor assembly for securing tissue to bone.

Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

SUMMARY

In one aspect, the present disclosure relates to an anchor assembly. The anchor assembly includes an anchor defining a cavity and an opening to the cavity and an insertion member configured for arrangement within the anchor cavity. The insertion member includes a body having a proximal end portion and a flat distal end portion, and a head coupled to the proximal end portion of the body. The anchor includes protrusions located on an outer surface of the anchor, wherein the protrusions are configured to facilitate loading of a flexible member into the anchor. In an embodiment, the anchor assembly further includes a transverse through hole extending through the anchor. In another embodiment, the anchor assembly further includes at least two slots on an outer surface of the anchor, wherein the slots extend from the transverse through hole to a proximal portion of the anchor. In yet another embodiment, the anchor includes barbs on an outer surface of the body, wherein the barbs are intersected by the slots.

In a further embodiment, at least one flexible member, which may be a suture, is disposed within the through hole. In yet a further embodiment, a plurality of flexible members are disposed within the through hole. In yet an even further embodiment, the cavity includes threads. In an embodiment, the insertion member body includes threads, wherein the threads are configured for engagement with the threads of the cavity when the insertion member is arranged within the cavity. In another embodiment, the cavity extends into the through hole. In yet another embodiment, the head is configured for engagement with a delivery device. In a further embodiment, the insertion member is arranged within the anchor cavity such that the insertion member secures the flexible member in the through hole.

In another aspect, the present disclosure relates to a method of tissue repair. The method includes inserting a first anchor into bone, the first anchor having a flexible member coupled thereto; passing ends of the flexible member through the tissue; providing a second anchor defining a cavity and an opening to the cavity and a transverse through hole extending through the anchor; passing at least one end of the flexible member through the through hole of the second anchor; placing the second anchor into bone; providing an insertion member including a body having a proximal end portion and a flat distal end portion, and a head coupled to the proximal end portion of the body; and placing the insertion member within the anchor cavity of the second anchor to secure the flexible member in the through hole and the tissue to the bone.

In an embodiment, the method further includes tensioning the flexible member before placing the insertion member within the anchor cavity. In another embodiment, the method further includes moving the insertion member away from the through hole, tensioning the flexible member, and moving the insertion member back toward the through hole to resecure the flexible member in the through hole. In yet another embodiment, the second anchor includes protrusions, wherein the protrusions create paths in a wall of the bone when the second anchor is inserted into the bone. The paths allow the flexible member to slide through the second anchor when the second anchor is located in the bone.

In yet another aspect, the present disclosure relates to an anchor assembly. The anchor assembly includes an anchor defining a proximal portion, a distal portion, and an inner cavity; and an insertion member configured for arrangement within the inner cavity. The anchor includes barbs located on the proximal portion and protrusions located on the distal portion, wherein the protrusions are configured to facilitate loading of a flexible member into the anchor. In an embodiment, the insertion member includes a proximal end portion and a flat distal end portion.

In still another aspect, an anchoring system includes an anchor with a longitudinal axis extending along a length of the anchor and a delivery device. The anchor may include an anchor body and an insertion member. The anchor body may more specifically include a proximal end positioned along the longitudinal axis, a distal end positioned along the longitudinal axis and opposite from the proximal end, a cavity positioned along the longitudinal axis between the proximal end and the distal end, an opening to the cavity at the proximal end of the anchor body, a transverse hole into the cavity, wherein the transverse hole includes a proximal edge and a distal edge, and wherein the cavity extends distal of the distal edge of the transverse hole and proximal of the proximal edge of the transverse hole. The insertion member may include an end having a substantially flat profile sized and configured to be moved within the cavity such that the insertion member, as measured from the substantially flat profile to another point along the insertion member, covers the transverse hole from a point proximal of the proximal edge of the transverse hole to a point distal of the distal edge of the transverse hole. The delivery device may be configured to couple with the anchor and move the insertion member relative to the anchor body along the longitudinal axis.

In an aspect, an anchoring system includes an anchor with a longitudinal axis extending along a length of the anchor and a delivery device. The anchor may include an anchor body and an insertion member. The anchor body may include a proximal end positioned along the longitudinal axis, a distal end positioned along the longitudinal axis and opposite from the proximal end, a cavity positioned along the longitudinal axis between the proximal end and the distal end, an opening to the cavity at the proximal end of the anchor body, a transverse hole into the cavity, wherein the transverse hole includes a proximal edge and a distal edge, and wherein the cavity has a working diameter that extends distal of the distal edge of the transverse hole and proximal of the proximal edge of the transverse hole. The insertion member may have a minimum diameter along a length of the insertion member sized to substantially fill the working diameter of the cavity from a point proximal of the proximal edge of the transverse hole to a point distal of the distal edge of the transverse hole. The delivery device may be configured to couple with the anchor and move the insertion member relative to the anchor body along the longitudinal axis.

Embodiments include an anchoring system having an anchor with a longitudinal axis extending along a length of the anchor and a delivery device. The anchor may include an anchor body and an insertion member. The anchor body may include a proximal end positioned along the longitudinal axis, a distal end positioned along the longitudinal axis and opposite from the proximal end, a cavity positioned along the longitudinal axis between the proximal end and the distal end, an opening to the cavity at the proximal end of the anchor body, a transverse hole into the cavity, wherein the transverse hole includes a proximal edge and a distal edge, and wherein the cavity extends distal of the distal edge of the transverse hole and proximal of the proximal edge of the transverse hole. The insertion member may be sized and configured to be moved within the cavity to cover the transverse hole, wherein the insertion member includes a typical outer body diameter, wherein the typical outer body diameter is smaller than a diameter of any threads on the insertion member and smaller than a diameter of any head of the insertion member and larger than a dimension of the transverse hole into the cavity that is substantially perpendicular to the longitudinal axis of the anchor, and wherein the anchor is sized and configured such that the typical body diameter of the insertion member fits within the cavity from a point proximal of the proximal edge of the transverse hole to a point distal of the distal edge of the transverse hole. The delivery device may be configured to couple with the anchor and move the insertion member relative to the anchor body along the longitudinal axis.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIGS. 4A-4D show use of the anchor assembly of the present disclosure in repairing tissue.

DETAILED DESCRIPTION OF THE EMBODIMENTS

The following description of the preferred embodiment(s) is merely exemplary in nature and is in no way intended to limit the disclosure, its application, or uses.

Figure 1:
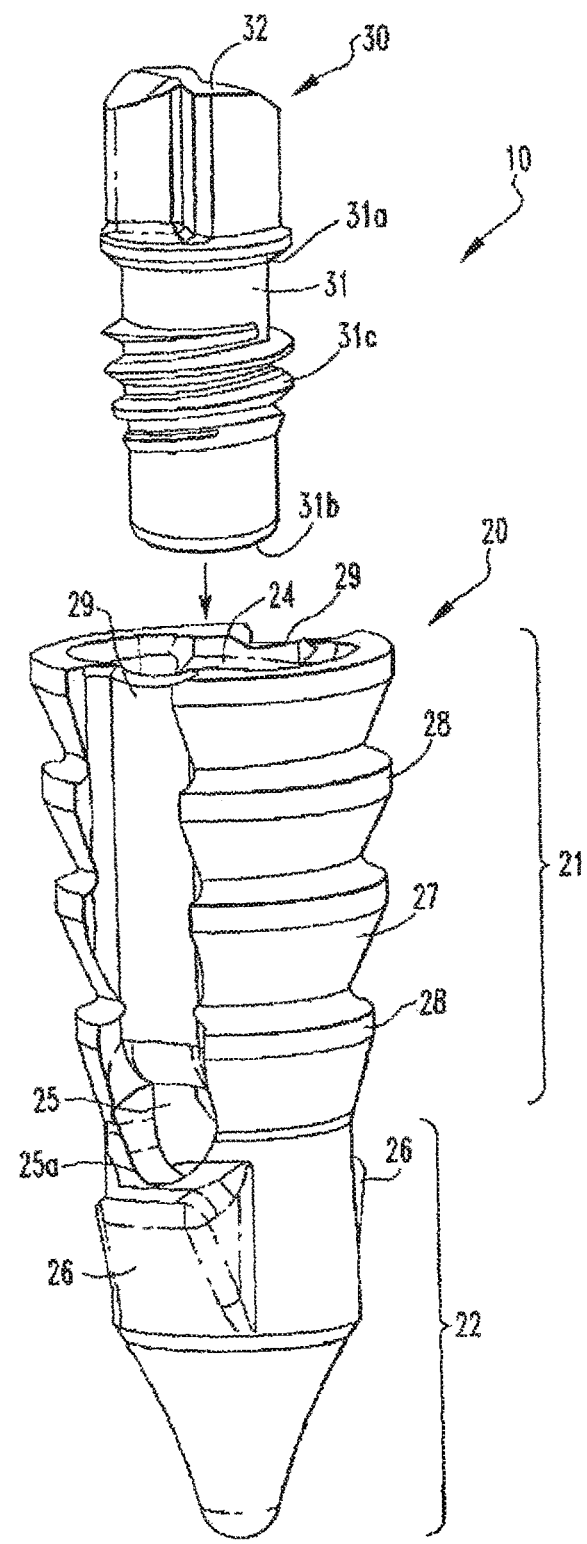
FIG. 1 shows an exploded view of the anchor assembly of the present disclosure.
Figure 2:
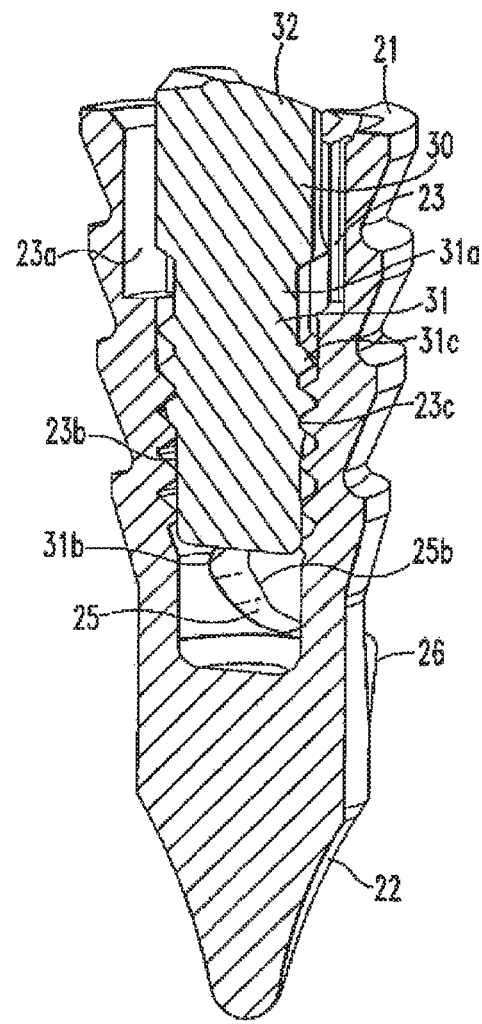
FIG. 2 shows a cross-sectional view of the anchor assembly of the present disclosure.
Figure 3:
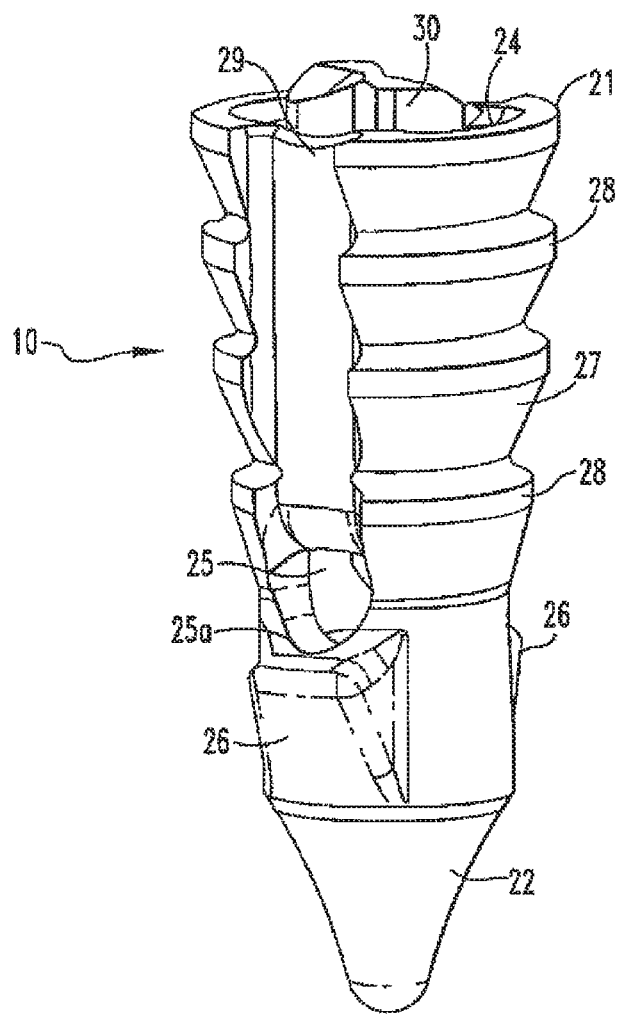
FIG. 3 shows a front view of the anchor assembly of the present disclosure.

FIGS. 1-3 show the anchor assembly 10 of the present disclosure. The assembly 10 includes the anchor 20 and the insertion member 30, The anchor 20 includes a proximal portion 21, a distal portion 22, and an inner cavity 23. An opening 24 to the cavity 23 is located at the proximal portion 21 of the anchor 20. A transverse through hole 25 is located between the proximal and distal portions 21, 22 and extends through the anchor 20. Openings 25a, b are located at each end of the through hole 25. Located below each opening 25a, b is a protrusion 26. The protrusions 26 facilitate loading of a flexible member, such as a suture, through the through hole 25, and allow for the creation of a path in the wall of a bone hole when the anchor 20 is inserted into bone hole, as will be further described below. The outer surface 27 of the proximal portion 21 also includes barbs 28 for substantially reducing the possibility of removal of the anchor 20 when inserted into bone, as will be further described below. The outer surface 27 also includes slots 29 extending from the openings 25a, b of the through hole 25 to the proximal portion 21 of the anchor 20. The slots 29 intersect the barbs 28 and are configured for housing of the suture after positioning of the anchor 20 in bone, as further described below. As shown in FIG. 2, the cavity 23 extends into the through hole 25 and includes a proximal portion 23a and a threaded distal portion 23b for receipt of the insertion member 30, as will be further described below.

The insertion member 30 includes a body 31, having a proximal end portion 31a and a flat distal end portion 31b, and a head 32 coupled to the proximal end portion 31a. The head 32 is configured for engagement with a delivery tool and the body 31 includes threads 31c that are configured for engagement with the threads 23c of the cavity 23 when the insertion member is arranged within the cavity 23, as shown in FIG. 2.

The anchor 10 of the present disclosure may be used in conjunction with another anchor to repair soft tissue. FIGS. 4A-4D show the anchor assembly 10 in use during arthroscopic repair of the rotator cuff. However, the anchor assembly 10 may be used in the repair of soft tissue in other parts of the body. FIG. 4A shows a first anchor 40 that has been inserted into the lateral aspect of a bone 50, such as a humeral bone. The anchor 40, which has a flexible member 60, such as a suture, coupled thereto is inserted into the bone 50, a soft tissue 70, such as a rotator cuff tendon, is placed on the bone 50 to be located adjacent to the anchor 40, and the ends 61 of the flexible member 60 are placed through the soft tissue 70.

Next, at least one end 61 of the flexible member 60 is passed through the transverse through hole 25 of a second anchor, such as the anchor 20 of the present disclosure, and the anchor 20 is subsequently placed into a previously drilled hole 51 in the medial aspect of the bone 50, as shown in FIG. 4B, such that the flexible member 60 is housed within the transverse through hole 25 and both slots 29 of the anchor 20 and the ends 61 extend out of the hole 51. The anchor 20 is advanced into the hole 50 in an axially-oriented manner by tapping on the end of a delivery tool (not shown) that is used to deliver the anchor 20 into the hole 51. FIGS.

4B-4D show spaces between the outer surface 27 of the anchor 20 and the walls 52 of the hole 51. However, the diameter of the hole 51 will be sized such that the barbs 28 of the anchor 20 will abut the walls 52, and most likely extend through the walls 52 and into the bone 50, in order to substantially reduce the possibility of anchor removal. In addition, due to the hole diameter, the protrusions 26 located below the openings 25a, b create a path (not shown) in the wall of the bone hole 51 when the anchor 20 is inserted into hole 51. This path allows the suture 60 to slide when through the anchor 20 when the anchor 20 is located within the hole 51.

After placement of the anchor 20 into the hole 51, the ends 61 of the flexible member 60 may be pulled to provide a preferred amount of tension on the flexible member 60 and the soft tissue 70. This tension on the flexible member 60 can be seen in FIGS. 4C-D, especially when comparing these figures to FIG. 4B. The insertion member 30 is subsequently placed in the anchor cavity 23 in a rotary manner, via a delivery tool 80, to secure the flexible member 60 in the through hole 25 and the tissue 70 to the bone 50. The insertion member 30 may be removed from the cavity 23 to re-tension the flexible member 60 and then replaced within the cavity 23 to re-secure the flexible member 60 in the through hole 25.

The components of the anchor assembly 10 and the first anchor 40 are made from a bioabsorbable polymer material via an injection molding process. However, other materials and processes may be used. In addition, the suture material is made from a bioabsorbable polymer material, but other material may be used. Also, the initial anchor, such as the first anchor 40 shown above, may include more than one suture and the sutures may be secured together at one attachment point, such as within the second anchor 20 shown above, or independently at more than one attachment point. Furthermore, the outer surface 27 of the anchor 20 may include features other than barbs 28 to reduce the possibility of removal of the anchor 20 and the barbs 28 may extend the entire length or a partial length of the anchor 20. Similarly, the body 31 of the insertion member 30 and the cavity 23 of the anchor 20 may include features other than threads to facilitate insertion and removal of the insertion member 30 and the threads may extend the entire length or a partial length of the body 31 and cavity 23. Also, for the purposes of this disclosure, the through hole 25 is located between the proximal 21 and distal 22 portions, but may be located anywhere along the length of the anchor 20.

The anchor assembly 10 of the present disclosure allows a surgeon to load a suture from a previously placed anchor and secure the suture in the assembly 10 at a preferred tension. In addition, the assembly 10 allows the tension on the suture to be adjusted with tactile feedback. Furthermore, the assembly allows for one or more sutures to be secured together at one attachment point, such as described above with the second anchor 20, or independently at several attachment points. This allows for a large area of contact between the tissue and the bone and results in a better repair.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An anchoring system comprising:
   an anchor with a longitudinal axis extending along a length of the anchor, the anchor comprising:
      an anchor body comprising:
         a proximal end positioned along the longitudinal axis,
         a distal end positioned along the longitudinal axis and opposite from the proximal end,
         a cavity positioned along the longitudinal axis between the proximal end and the distal end,
         an opening to the cavity at the proximal end of the anchor body, and
         a transverse hole into the cavity, wherein the transverse hole includes a proximal edge and a distal edge, and wherein the cavity extends distal of the distal edge of the transverse hole and proximal of the proximal edge of the transverse hole, and
      an insertion member with a distal end having a substantially flat profile sized and configured to be moved within the cavity such that the insertion member, as measured from the substantially flat profile to another point along the insertion member, covers the transverse hole from a point proximal of the proximal edge of the transverse hole to a point distal of the distal edge of the transverse hole; and
   a delivery device configured to couple with the anchor and move the insertion member relative to the anchor body along the longitudinal axis.

2. The anchoring system of claim 1 wherein the transverse hole into the cavity goes through each side of the anchor body and goes through the cavity between each side of the anchor body.

3. The anchoring system of claim 1 wherein an interior portion of the cavity in the anchor body includes ridges.

4. The anchoring system of claim 3 wherein the ridges are formed by threads within the cavity.

5. The anchoring system of claim 1 wherein the anchor body includes one or more barbs on an exterior of the anchor body positioned to resist proximal movement of the anchor from a bone.

6. The anchoring system of claim 1 wherein the anchor body includes one or more protrusions on an exterior of the anchor body located distal of the transverse hole into the cavity.

7. The anchoring system of claim 1 wherein the distal end of the insertion member having a substantially flat profile is a substantially solid substantially flat end.

8. The anchoring system of claim 1 wherein the insertion member is sized and configured to be moved distally and proximally within the cavity of the anchor body.

9. The anchoring system of claim 1 wherein the insertion member with a distal end having a substantially flat profile is sized and configured to be moved distally within the cavity of the anchor body such that the insertion member covers the transverse hole from a point proximal of the proximal edge to a point distal of the distal edge, wherein after such covering movement the distal end having the substantially flat profile is located at the point distal of the distal edge.

10. The anchoring system of claim 1 wherein the delivery device includes a first portion configured to couple to the anchor body and a second portion configured to couple to the insertion member.

11. The anchoring system of claim 1 wherein the delivery device is configured to move the insertion member relative to the anchor body along the longitudinal axis by rotating the insertion member relative to the anchor body.

12. The anchoring system of claim 1, further comprising a flexible member sized to be passed into the transverse hole in the anchor body and to be fixed relative to the anchor body when the insertion member is moved within the cavity such that the insertion member covers the transverse hole from a point proximal of the proximal edge to a point distal of the distal edge.

13. An anchoring system comprising:
an anchor with a longitudinal axis extending along a length of the anchor, the anchor comprising:
an anchor body comprising:
a proximal end positioned along the longitudinal axis,
a distal end positioned along the longitudinal axis and opposite from the proximal end,
a cavity positioned along the longitudinal axis between the proximal end and the distal end,
an opening to the cavity at the proximal end of the anchor body, and
a transverse hole into the cavity, wherein the transverse hole includes a proximal edge and a distal edge, and wherein the cavity has a working diameter that extends distal of the distal edge of the transverse hole and proximal of the proximal edge of the transverse hole, and
an insertion member with a minimum diameter along a length of the insertion member sized to substantially fill the working diameter of the cavity from a point proximal of the proximal edge of the transverse hole to a point distal of the distal edge of the transverse hole,
wherein the working diameter of the cavity is substantially the same at the point proximal of the proximal edge of the transverse hole and at the point distal of the distal edge of the transverse hole where the minimum diameter substantially fills the working diameter of the cavity;
a delivery device configured to couple with the anchor and move the insertion member relative to the anchor body along the longitudinal axis; and
a flexible member sized to be passed into the transverse hole in the anchor body and to be fixed relative to the anchor body when the insertion member is moved within the cavity such that the insertion member covers the transverse hole from a point proximal of the proximal edge to a point distal of the distal edge.

14. The anchoring system of claim 13 wherein the transverse hole into the cavity goes through each side of the anchor body and goes through the cavity between each side of the anchor body.

15. The anchoring system of claim 13 wherein an interior portion of the cavity in the anchor body includes ridges.

16. The anchoring system of claim 15 wherein the ridges are formed by threads within the cavity.

17. The anchoring system of claim 13 wherein the anchor body includes one or more barbs on an exterior of the anchor body positioned to resist proximal movement of the anchor from a bone.

18. The anchoring system of claim 13 wherein the anchor body includes one or more protrusions on an exterior of the anchor body located distal of the transverse hole into the cavity.

19. The anchoring system of claim 13 wherein the insertion member includes an end having a substantially flat profile.

20. The anchoring system of claim 19 wherein the end of the insertion member having a substantially flat profile is a substantially solid substantially flat end.

21. The anchoring system of claim 19 wherein the end having a substantially flat profile is a distal end of the insertion member.

22. The anchoring system of claim 19 wherein the insertion member with an end having a substantially flat profile is sized and configured to be moved distally within the cavity of the anchor body such that the insertion member covers the transverse hole from a point proximal of the proximal edge to a point distal of the distal edge, wherein after such covering movement the end having the substantially flat profile is located at the point distal of the distal edge.

23. The anchoring system of claim 13 wherein the delivery device includes a first portion configured to couple to the anchor body and a second portion configured to couple to the insertion member.

24. The anchoring system of claim 13 wherein the delivery device is configured to move the insertion member relative to the anchor body along the longitudinal axis by rotating the insertion member relative to the anchor body.

25. An anchoring system comprising:
an anchor with a longitudinal axis extending along a length of the anchor, the anchor comprising:
an anchor body comprising:
a proximal end positioned along the longitudinal axis,
a distal end positioned along the longitudinal axis and opposite from the proximal end,
a cavity positioned along the longitudinal axis between the proximal end and the distal end,
an opening to the cavity at the proximal end of the anchor body, and
a transverse hole into the cavity, wherein the transverse hole includes a proximal edge and a distal edge, and wherein the cavity extends distal of the distal edge of the transverse hole and proximal of the proximal edge of the transverse hole, and
an insertion member sized and configured to be moved within the cavity to cover the transverse hole, wherein the insertion member includes a typical outer body diameter, wherein the typical outer body diameter is smaller than a diameter of any threads on the insertion member and smaller than a diameter of any head of the insertion member and larger than a maximum dimension of the transverse hole into the cavity that is substantially perpendicular to the longitudinal axis of the anchor, and wherein the anchor is sized and configured such that the typical outer body diameter of the insertion member fits within the cavity from a point proximal of the proximal edge of the transverse hole to a point distal of the distal edge of the transverse hole; and
a delivery device configured to couple with the anchor and move the insertion member relative to the anchor body along the longitudinal axis; and
a flexible member sized to be passed into the transverse hole in the anchor body and to be fixed relative to the anchor body when the insertion member is moved within the cavity such that the insertion member covers the transverse hole from a point proximal of the proximal edge to a point distal of the distal edge.

26. The anchoring system of claim 25 wherein the transverse hole into the cavity goes through each side of the anchor body and goes through the cavity between each side of the anchor body.

27. The anchoring system of claim 25 wherein an interior portion of the cavity in the anchor body includes ridges.

28. The anchoring system of claim 27 wherein the ridges are formed by threads within the cavity.

29. The anchoring system of claim 25 wherein a portion of the cavity proximal of the transverse hole includes threads.

30. The anchoring system of claim 25 wherein the anchor body includes one or more barbs on an exterior of the anchor body positioned to resist proximal movement of the anchor from a bone.

31. The anchoring system of claim 25 wherein the anchor body includes one or more protrusions on an exterior of the anchor body located distal of the transverse hole into the cavity.

32. The anchoring system of claim 25 wherein the insertion member includes an end having a substantially flat profile.

33. The anchoring system of claim 32 wherein the end of the insertion member having a substantially flat profile is a substantially solid substantially flat end.

34. The anchoring system of claim 32 wherein the end having a substantially flat profile is a distal end of the insertion member.

35. The anchoring system of claim 32 wherein the diameter of the end of the insertion member having a substantially flat profile is substantially the same diameter as the typical outer body diameter.

36. The anchoring system of claim 32 wherein the insertion member with an end having a substantially flat profile is sized and configured to be moved distally within the cavity of the anchor body such that the insertion member covers the transverse hole from a point proximal of the proximal edge to a point distal of the distal edge, wherein after such covering movement the end having the substantially flat profile is located at the point distal of the distal edge.

37. The anchoring system of claim 25 wherein the delivery device includes a first portion configured to couple to the anchor body and a second portion configured to couple to the insertion member.

38. The anchoring system of claim 25 wherein the delivery device is configured to move the insertion member relative to the anchor body along the longitudinal axis by rotating the insertion member relative to the anchor body.

39. An anchoring system comprising:
  an anchor with a longitudinal axis extending along a length of the anchor, the anchor comprising:
    an anchor body comprising:
      a proximal end positioned along the longitudinal axis,
      a distal end positioned along the longitudinal axis and opposite from the proximal end,
      a cavity positioned along the longitudinal axis between the proximal end and the distal end,
      an opening to the cavity at the proximal end of the anchor body, and
      a transverse hole into the cavity, wherein the transverse hole includes a proximal edge and a distal edge, and wherein the cavity has a working diameter that extends distal of the distal edge of the transverse hole and proximal of the proximal edge of the transverse hole, and
    an insertion member with a minimum diameter along a length of the insertion member sized to substantially fill the working diameter of the cavity from a point proximal of the proximal edge of the transverse hole to a point distal of the distal edge of the transverse hole, the insertion member including an end having a substantially flat profile;
    wherein the working diameter of the cavity is substantially the same at the point proximal of the proximal edge of the transverse hole and at the point distal of the distal edge of the transverse hole where the minimum diameter substantially fills the working diameter of the cavity; and
  a delivery device configured to couple with the anchor and move the insertion member relative to the anchor body along the longitudinal axis.

40. The anchoring system of claim 39 wherein the transverse hole into the cavity goes through each side of the anchor body and goes through the cavity between each side of the anchor body.

41. The anchoring system of claim 39 wherein an interior portion of the cavity in the anchor body includes ridges.

42. The anchoring system of claim 41 wherein the ridges are formed by threads within the cavity.

43. The anchoring system of claim 39 wherein the anchor body includes one or more barbs on an exterior of the anchor body positioned to resist proximal movement of the anchor from a bone.

44. The anchoring system of claim 39 wherein the anchor body includes one or more protrusions on an exterior of the anchor body located distal of the transverse hole into the cavity.

45. The anchoring system of claim 39 wherein the end of the insertion member having a substantially flat profile is a substantially solid substantially flat end.

46. The anchoring system of claim 39 wherein the end having a substantially flat profile is a distal end of the insertion member.

47. The anchoring system of claim 39 wherein the insertion member with an end having a substantially flat profile is sized and configured to be moved distally within the cavity of the anchor body such that the insertion member covers the transverse hole from a point proximal of the proximal edge to a point distal of the distal edge, wherein after such covering movement the end having the substantially flat profile is located at the point distal of the distal edge.

48. The anchoring system of claim 39 wherein the delivery device includes a first portion configured to couple to the anchor body and a second portion configured to couple to the insertion member.

49. The anchoring system of claim 39 wherein the delivery device is configured to move the insertion member relative to the anchor body along the longitudinal axis by rotating the insertion member relative to the anchor body.

50. The anchoring system of claim 39, further comprising a flexible member sized to be passed into the transverse hole in the anchor body and to be fixed relative to the anchor body when the insertion member is moved within the cavity such that the insertion member covers the transverse hole from a point proximal of the proximal edge to a point distal of the distal edge.

51. An anchoring system comprising:
  an anchor with a longitudinal axis extending along a length of the anchor, the anchor comprising:
    an anchor body comprising:

a proximal end positioned along the longitudinal axis, a distal end positioned along the longitudinal axis and opposite from the proximal end, a cavity positioned along the longitudinal axis between the proximal end and the distal end, an opening to the cavity at the proximal end of the anchor body, and a transverse hole into the cavity, wherein the transverse hole includes a proximal edge and a distal edge, and wherein the cavity extends distal of the distal edge of the transverse hole and proximal of the proximal edge of the transverse hole, and an insertion member sized and configured to be moved within the cavity to cover the transverse hole, wherein the insertion member includes a typical outer body diameter, wherein the typical outer body diameter is smaller than a diameter of any threads on the insertion member and smaller than a diameter of any head of the insertion member and larger than a maximum dimension of the transverse hole into the cavity that is substantially perpendicular to the longitudinal axis of the anchor, wherein the anchor is sized and configured such that the typical outer body diameter of the insertion member fits within the cavity from a point proximal of the proximal edge of the transverse hole to a point distal of the distal edge of the transverse hole, and wherein the insertion member includes an end having a substantially flat profile; and a delivery device configured to couple with the anchor and move the insertion member relative to the anchor body along the longitudinal axis.

52. The anchoring system of claim 51 wherein the transverse hole into the cavity goes through each side of the anchor body and goes through the cavity between each side of the anchor body.

53. The anchoring system of claim 51 wherein an interior portion of the cavity in the anchor body includes ridges.

54. The anchoring system of claim 53 wherein the ridges are formed by threads within the cavity.

55. The anchoring system of claim 51 wherein a portion of the cavity proximal of the transverse hole includes threads.

56. The anchoring system of claim 51 wherein the anchor body includes one or more barbs on an exterior of the anchor body positioned to resist proximal movement of the anchor from a bone.

57. The anchoring system of claim 51 wherein the anchor body includes one or more protrusions on an exterior of the anchor body located distal of the transverse hole into the cavity.

58. The anchoring system of claim 51 wherein the end of the insertion member having a substantially flat profile is a substantially solid substantially flat end.

59. The anchoring system of claim 51 wherein the end having a substantially flat profile is a distal end of the insertion member.

60. The anchoring system of claim 51 wherein the diameter of the end of the insertion member having a substantially flat profile is substantially the same diameter as the typical outer body diameter.

61. The anchoring system of claim 51 wherein the insertion member with an end having a substantially flat profile is sized and configured to be moved distally within the cavity of the anchor body such that the insertion member covers the transverse hole from a point proximal of the proximal edge to a point distal of the distal edge, wherein after such covering movement the end having the substantially flat profile is located at the point distal of the distal edge.

62. The anchoring system of claim 51 wherein the delivery device includes a first portion configured to couple to the anchor body and a second portion configured to couple to the insertion member.

63. The anchoring system of claim 51 wherein the delivery device is configured to move the insertion member relative to the anchor body along the longitudinal axis by rotating the insertion member relative to the anchor body.

64. The anchoring system of claim 51, further comprising a flexible member sized to be passed into the transverse hole in the anchor body and to be fixed relative to the anchor body when the insertion member is moved within the cavity such that the insertion member covers the transverse hole from a point proximal of the proximal edge to a point distal of the distal edge.

\* \* \* \* \*